US008900641B2

(12) United States Patent
Ramesh et al.

(10) Patent No.: US 8,900,641 B2
(45) Date of Patent: Dec. 2, 2014

(54) ANTIMICROBIAL COMPOSITION

(75) Inventors: Manian Ramesh, Barrington Hill, IL (US); Cathy C. Doucette, Sugar Grove, IL (US); Andrew J. Cooper, Oswego, IL (US)

(73) Assignee: Nalco Company, Naperville, IL (US)

( * ) Notice: Subject to any disclaimer, the term of this patent is extended or adjusted under 35 U.S.C. 154(b) by 780 days.

(21) Appl. No.: 12/371,162

(22) Filed: Feb. 13, 2009

(65) Prior Publication Data

US 2009/0214672 A1 Aug. 27, 2009

Related U.S. Application Data

(63) Continuation-in-part of application No. 11/617,318, filed on Dec. 28, 2006, now abandoned.

(51) Int. Cl.
*A01N 59/08* (2006.01)
*A61K 31/74* (2006.01)
*A01N 25/00* (2006.01)
*A01N 59/00* (2006.01)

(52) U.S. Cl.
USPC ......... 424/661; 424/78.09; 424/405; 424/719

(58) Field of Classification Search
CPC ... A01N 2300/00; A01N 65/00; A01N 25/04; A01N 33/12; C02F 2303/04; C02F 2209/29
USPC ............... 424/661, 78.09, 405, 719
See application file for complete search history.

(56) References Cited

U.S. PATENT DOCUMENTS

| | | | |
|---|---|---|---|
| 4,189,381 A * | 2/1980 | Laferty et al. ............ 210/665 |
| 4,929,655 A | 5/1990 | Takeda et al. |
| 4,988,444 A | 1/1991 | Applegate et al. |
| 5,006,590 A | 4/1991 | Takeda et al. |
| 5,292,793 A | 3/1994 | Ramesh et al. |
| 5,374,536 A * | 12/1994 | Robertson ............ 435/26 |
| 5,435,922 A | 7/1995 | Ramesh et al. |
| 5,466,338 A | 11/1995 | Pearson |
| 5,597,858 A | 1/1997 | Ramesh et al. |
| 5,597,859 A | 1/1997 | Hurlock et al. |
| 5,605,970 A | 2/1997 | Selvarajan |
| 5,837,776 A | 11/1998 | Selvarajan et al. |
| 5,891,304 A | 4/1999 | Shing |
| 5,938,937 A | 8/1999 | Sparapany |
| 5,976,386 A | 11/1999 | Barak |
| 5,985,992 A | 11/1999 | Chen |
| 6,007,679 A | 12/1999 | Nagarajan et al. |
| 6,019,904 A | 2/2000 | Shing et al. |
| 6,059,930 A | 5/2000 | Shing et al. |
| 6,071,379 A | 6/2000 | Shing et al. |
| 6,132,628 A | 10/2000 | Barak |
| 6,171,505 B1 | 1/2001 | Maury et al. |
| 6,217,778 B1 | 4/2001 | Shing et al. |
| 6,238,521 B1 | 5/2001 | Shing et al. |
| 6,258,279 B1 | 7/2001 | Shah et al. |
| 6,265,477 B1 | 7/2001 | Hurlock |
| 6,313,246 B1 | 11/2001 | Carter et al. |
| 6,331,229 B1 | 12/2001 | Shing et al. |
| 6,413,433 B1 | 7/2002 | Maury et al. |
| 6,432,271 B1 | 8/2002 | Shing et al. |
| 6,478,973 B1 | 11/2002 | Barak |
| 6,592,718 B1 | 7/2003 | Shing et al. |
| 6,605,674 B1 | 8/2003 | Whipple et al. |
| 6,709,551 B2 | 3/2004 | Coffey et al. |
| 6,773,607 B2 | 8/2004 | Russell |
| 7,067,063 B2 | 6/2006 | Barak |
| 2003/0121868 A1 | 7/2003 | Barak |
| 2003/0132173 A1 | 7/2003 | Barak |
| 2005/0194324 A1 | 9/2005 | Barak |
| 2006/0084771 A1 | 4/2006 | Shing et al. |

FOREIGN PATENT DOCUMENTS

EP 630909 12/1994
EP 657478 6/1995

OTHER PUBLICATIONS

Chen et al., Biomacromolecules, 2000, 1, 473-480.*
Chamorey et al., J. Hospital Infection, 1999, 41, 45-49.*
Beck J. et al. 1986. Preformed monochloramine used as a post-disinfectant in drinking water treatment. Aqua I, 25-33.
Morris, J.C. 1967. "Kinetics of Reactions Between Aqueous Chlorine and Nitrogen Compounds" Principles and Applications of Water Chemistry. S.D. Faust and J.V. Hunter (editors). John Wiley and Sons, New York, N.Y.
United States Environmental Protection Agency. 1999. Alternative Oxidants and Disinfectants Manual, Chapter 6 "Chloramine". EPA publication No. 815-R-99-014.
Weil, I. and J.C. Morris. 1949. "Kinetic Studies on the Chloramines. The Rates of Formation of Monochloramine, N-Chlormethylamine and N-Chlordimethylamine." *J. Amer. Chem. Soc.* 71:1664.

* cited by examiner

*Primary Examiner* — Abigail Fisher
(74) *Attorney, Agent, or Firm* — Benjamin E. Carlsen

(57) ABSTRACT

An antimicrobial composition prepared by mixing a polymer-ammonium salt formulation comprising one or more polymers and one or more ammonium salts with alkali and a chlorine source in a molar ratio of chlorine (as $Cl_2$) to ammonium ion of about 1:10 to about 10:1 and methods of using the composition to control biofouling of aqueous systems.

15 Claims, No Drawings

ANTIMICROBIAL COMPOSITION

CROSS REFERENCE TO RELATED APPLICATIONS

This application is a continuation in part to U.S. patent application Ser. No. 11/617,318, which was filed on Dec. 28, 2006 now abandoned, from which filing priority is hereby claimed and the disclosure of which is hereby incorporated by reference.

TECHNICAL FIELD

This invention relates to compositions used in biofouling control in industrial water systems. More specifically, this invention relates to a biocidal composition prepared by mixing a formulation comprising one or more polymers and one or more ammonium salts with alkali and a chlorine source and use of the composition in biofouling control in industrial water systems.

BACKGROUND OF THE INVENTION

Chlorine is commonly used in aqueous systems for controlling the growth of microorganisms. For example, in papermaking processes, chlorine is a preferred halogen biocide due to its low cost, broad spectrum and fast biocidal activity, and convenience of monitoring and control. However, use of chlorine also results in increased corrosion of system components, degradation of felts, destruction of other water treatment additives, and negative impacts on paper-making additives such as dyes and brighteners.

To improve the biocidal properties of chlorine, particularly against biofilm and filamentous organisms, and to decrease the negative impact of chlorine use, free chlorine can be stabilized using nitrogenous compounds to form chloramines. Chloramine formation and chloramine's properties as a disinfectant have been known since the early 1900's, and the relative reaction rates of chlorine with amine-containing compounds versus ammonia were studied more that 50 years ago (Weil, I. and J. C. Morris. 1949. "Kinetic Studies on the Chloramines. The Rates of Formation of Monochloramine, N-Chlormethylamine and N-Chlordimethylamine." J. Amer. Chem. Soc. 71:1664). Chloramines are also approved and widely used for potable water distribution systems (United States Environmental Protection Agency. 1999. Alternative Oxidants and Disinfectants Manual, Chapter 6. EPA publication number 815-R-99-014).

The use of ammonium salts as practical compositions for stabilizing chlorine has also been known for many years. For example, Beck (J. Beck et al., Aqua I, 25-33, 1986) describes the use of pre-formed monochloramine for the post-disinfection of drinking water. In this work, chloramines are formed by mixing ammonium sulfate and hypochlorite solution at a concentration of 1000 ppm and adjusting the pH to 7.5 before the point of dosage to avoid carbonate precipitation. This is typical of chloramines applications, in which the usual ammonium ion sources are ammonia, ammonium chloride and ammonium sulfate.

Additional examples of using chloramines to control biofouling include U.S. Pat. No. 4,988,444, which describes the use of chloramines to prevent microbial fouling on reverse osmosis membranes, U.S. Pat. No. 6,773,607 which describes using chloramine formed in ballast water by adding aqueous ammonia or an ammonium salt, and sodium or calcium hypochlorite to the ballast water and U.S. Pat. Nos. 5,976,386, 6,132,628, 6,478,973 and 7,067,063, and references cited therein which disclose mixing an oxidant, preferably an active chlorine donor and still more preferably sodium hypochlorite and an ammonium salt, preferably chosen among halides, sulfates and nitrates, and adding the biocidal concentrate immediately to the aqueous system to be treated.

SUMMARY OF THE INVENTION

This invention is an antimicrobial composition prepared by mixing an aqueous polymer-ammonium salt formulation comprising one or more polymers and one or more ammonium salts with a chlorine source in a molar ratio of chlorine (as $Cl_2$) to ammonium ion of about 1:10 to about 10:1 and sufficient alkali to result in a composition which exhibits effective antimicrobial activity in a system being treated.

In another aspect, this invention is a method of inhibiting the growth of microorganisms in an aqueous system comprising treating the system with an antimicrobial composition prepared by mixing an aqueous polymer-ammonium salt formulation comprising one or more polymers and one or more ammonium salts with a chlorine source in a molar ratio of chlorine (as $Cl_2$) to ammonium ion of about 1:10 to about 10:1 and sufficient alkali to result in a composition which exhibits effective antimicrobial activity in a system being treated.

The composition of this invention comprises a mixture of polymer, free chlorine and stable chloramines. This invention, therefore, allows for the selection of polymers in order to obtain a known property or performance in water treatment or papermaking applications derived from the polymers in addition to the biocidal properties of the composition.

DETAILED DESCRIPTION OF THE INVENTION

As used herein, "anionic monomer" means a monomer as defined herein which possesses a net negative charge. Representative anionic monomers include acrylic acid, and it's salts, including, but not limited to sodium acrylate, and ammonium acrylate, methacrylic acid, and it's salts, including, but not limited to sodium methacrylate, and ammonium methacrylate, 2-acrylamido-2-methylpropanesulfonic acid (AMPS), the sodium salt of AMPS, sodium vinyl sulfonate, styrene sulfonate, maleic acid, and it's salts, including, but not limited to the sodium salt, and ammonium salt, sulfonate itaconate, sulfopropyl acrylate or methacrylate or other water-soluble forms of these or other polymerisable carboxylic or sulphonic acids. Sulfomethylated acrylamide, allyl sulfonate, itaconic acid, acrylamidomethylbutanoic acid, fumaric acid, vinylphosphonic acid, vinylsulfonic acid, allylphosphonic acid, sulfomethyalted acrylamide, phosphonomethylated acrylamide, and the like.

"Anionic polymer" means a polymer having an overall negative charge above a certain pH range. The anionic polymer is prepared by vinyl addition polymerization of one or more anionic monomers or by copolymerization of one or more anionic monomers with one or more nonionic, cationic or Zwitterionic monomers. Preferred anionic polymers include polymers and copolymers of acrylic acid, methacrylic acid, acrylamidomethylpropane sulfonic acid, N-vinyl formamide and acrylamide.

"Cationic Monomer" means a monomer as defined herein which possesses a net positive charge. Representative cationic monomers include dialkylaminoalkyl acrylates and methacrylates and their quaternary or acid salts, including, but not limited to, dimethylaminoethyl acrylate methyl chloride quaternary salt (DMAEA•MCQ), dimethylaminoethyl acrylate methyl sulfate quaternary salt, dimethylaminoethyl acrylate benzyl chloride quaternary salt (DMAEA•BCQ), dimethylaminoethyl acrylate sulfuric acid salt, dimethylaminoethyl acrylate hydrochloric acid salt, diethylaminoethyl acrylate, methyl chloride quaternary salt, dimethylaminoethyl methacrylate methyl chloride quaternary salt (DMAEM•MCQ), dimethylaminoethyl methacrylate methyl sulfate quaternary salt, dimethylaminoethyl methacrylate benzyl chloride quaternary salt, dimethylaminoethyl methacrylate sulfuric acid salt, dimethylaminoethyl methacrylate hydrochloric acid salt, diethylaminoethyl methacrylate methyl chloride quaternary salt, dimethylaminoethyl methacryloyl hydrochloric acid salt, dialkylaminoalkylacrylamides or methacrylamides and their quaternary or acid salts such as acrylamidopropyltrimethylammonium chloride, dimethylaminopropyl acrylamide methyl sulfate quaternary salt, dimethylaminopropyl acrylamide sulfuric acid salt, dimethylaminopropyl acrylamide hydrochloric acid salt, methacrylamidopropyltrimethylammonium chloride, dimethylaminopropyl methacrylamide methyl sulfate quaternary salt, dimethylaminopropyl methacrylamide sulfuric acid salt, dimethylaminopropyl methacrylamide hydrochloric acid salt, and diallyldialkylammonium halides such as diallyldiethylammonium chloride and diallyldimethyl ammonium chloride (DADMAC).

"Cationic polymer" means a polymer having an overall positive charge. The cationic polymer is typically prepared by vinyl addition polymerization of one or more cationic monomers, by copolymerization of one or more cationic monomers with one or more nonionic monomers, or by polymerization of the cationic monomers with one or more anionic monomers and optionally one or more nonionic monomers or zwitterionic monomers to produce an amphoteric polymer.

While the polymer may be formed initially as a cationic polymer, it is also possible to react certain non-ionic vinyl addition polymers to subsequently produce cationically charged polymers. Polymers of this type include those prepared through the reaction of polyacrylamide with dimethylamine and formaldehyde to produce a Mannich derivative.

"Monomer" means a polymerizable allylic, vinylic or acrylic compound. The monomer may be anionic, cationic, nonionic or Zwitterionic. Vinyl monomers are preferred, acrylic monomers are more preferred.

"Nonionic monomer" means a monomer as defined herein which is electrically neutral. Representative non-ionic, water-soluble monomers include acrylamide, methacrylamide, N-methylacrylamide, N,N-dimethylacrylamide, N,N-diethylacrylamide, N-isopropylacrylamide, N-vinylformamide, N-vinylmethylacetamide, N-vinylacetamide, N-methyl-N-vinylacetamide, dimethylhydroxypropyl(meth)acrylate, hydroxyethyl methacrylate, hydroxyethyl acrylate, hydroxypropyl acrylate, hydroxypropyl methacrylate, N-t-butylacrylamide, N-methylolacrylamide, vinyl acetate, acrylonitrile, 2-ethylhexyl acrylate, and the like.

"Zwitterionic monomer" means a polymerizable molecule containing cationic and anionic (charged) functionality in equal proportions, so that the molecule is net neutral overall. Representative zwitterionic monomers include N,N-dimethyl-N-acryloyloxyethyl-N-(3-sulfopropyl)-ammonium betaine, N,N-dimethyl-N-acrylamidopropyl-N-(2-carboxymethyl)-ammonium betaine, N,N-dimethyl-N-acrylamidopropyl-N-(3-sulfopropyl)-ammonium betaine, N,N-dimethyl-N-acrylamidopropyl-N-(2-carboxymethyl)-ammonium betaine, 2-(methylthio)ethyl methacryloyl-S-(sulfopropyl)-sulfonium betaine, 2-[(2-acryloylethyl) dimethylammonio]ethyl 2-methyl phosphate, 2-(acryloyloxyethyl)-2'-(trimethylammonium)ethyl phosphate, [(2-acryloylethyl)dimethylammonio]methyl phosphonic acid, 2-methacryloyloxyethyl phosphorylcholine (MPC), 2-[(3-acrylamidopropyl)dimethylammonio]methyl 2'-isopropyl phosphate (AAPI), 1-vinyl-3-(3-sulfopropyl)imidazolium hydroxide, (2-acryloxyethyl) carboxymethyl methylsulfonium chloride, 1-(3-sulfopropyl)-2-vinylpyridinium betaine, N-(4-sulfobutyl)-N-methyl-N,N-diallylamine ammonium betaine (MDABS), N,N-diallyl-N-methyl-N-(2-sulfoethyl)ammonium betaine, and the like.

"Zwitterionic polymer" means a polymer composed from zwitterionic monomers and, possibly, other non-ionic monomer(s), cationic monomers and/or anionic as disclosed in U.S. Pat. Nos. 6,709,551 and 6,313,246.

"RSV" stands for Reduced Specific Viscosity. Within a series of polymer homologs which are substantially linear and well solvated, "reduced specific viscosity (RSV)" measurements for dilute polymer solutions are an indication of polymer chain length and average molecular weight according to Paul J. Flory, in "Principles of Polymer Chemistry", Cornell University Press, Ithaca, N.Y., ©1953, Chapter VII, "Determination of Molecular Weights", pp. 266-316. The RSV is measured at a given polymer concentration and temperature and calculated as follows:

$$RSV = \frac{[(\eta/\eta_o) - 1]}{c}$$

$\eta$=viscosity of polymer solution, $\eta_o$=viscosity of solvent at the same temperature and c concentration of polymer in solution where the units of concentration "c" are (grams/100 ml or g/deciliter). Therefore, the units of RSV are dl/g. In this patent application, a 1.0 molar sodium nitrate solution is used for measuring RSV. The polymer concentration in this solvent is measured at about 0.045 g/dL. The RSV is measured at 30° C. The viscosities $\eta$ and $\eta_o$ are measured using a Cannon Ubbelohde semimicro dilution viscometer, size 75. The viscometer is mounted in a perfectly vertical position in a constant temperature bath adjusted to 30±0.02° C. The error inherent in the calculation of RSV is about 2 dl/grams. When two polymer homologs within a series have similar RSV's that is an indication that they have similar molecular weights.

The antimicrobial composition of this invention is prepared by mixing an aqueous polymer-ammonium salt formulation comprising one or more polymers and one or more ammonium salts with a chlorine source in a molar ratio of chlorine (as $Cl_2$) to ammonium ion of about 1:10 to about 10:1 and sufficient alkali to result in a pH of at least 7.

Suitable chlorine sources include any agent capable of providing free chlorine under the conditions described herein. In an embodiment, the chlorine source is chlorine gas, sodium hypochlorite, calcium hypochlorite, dichloroisocyanurate, trichloroisocyanurate, and the like. In another embodiment, the chlorine source is chlorine gas or sodium hypochlorite. In another embodiment, the chlorine source is sodium hypochlorite. In another embodiment, the chlorine source is an aqueous sodium hypochlorite solution having about 5 to about 15 percent of chlorine, based on $Cl_2$.

In an embodiment, polymers used in the aqueous polymer-ammonium salt formulation have a weight average molecular weight of at least about 100,000 g/mole.

In an embodiment, the aqueous polymer-ammonium salt formulation is an aqueous dispersion of one or more polymers in aqueous ammonium salt solution.

The aqueous dispersion of one or more polymers in aqueous ammonium salt solution may be prepared by polymerizing monomers in an aqueous continuous phase containing one or more ammonium salts. Representative examples of dispersion polymerization of water-soluble polymers in an aqueous continuous phase can be found in U.S. Pat. Nos. 5,605,970; 5,837,776; 5,985,992; 4,929,655; 5,006,590; 5,597,859; and 5,597,858 and in European Patent Nos. 183, 466; 657,478; and 630,909.

In a typical synthesis, the polymer dispersion is prepared by combining water, one or more ammonium salts, one or more water-soluble monomers, any polymerization additives such as chelants, pH buffers or chain transfer agents, and a water-soluble stabilizer polymer. In addition, further processing, structure modifying and/or stabilizing agents may be added to the mixture. All or a portion of this mixture is charged to a reactor equipped with a mixer, thermocouple, nitrogen purging tube, and water condenser. The solution is mixed vigorously, heated to the desired temperature, and then a water-soluble initiator is added. The solution is purged with nitrogen while maintaining temperature and mixing for several hours. During the course of the reaction, a discontinuous phase containing the water-soluble polymer is formed. A portion of the reaction mixture containing any combination of the starting materials may be added in a semi-batch fashion during the course of the polymerization to improve processing or affect polymer composition or molecular weight. After this time, the products are cooled to room temperature, and any post-polymerization additives are charged to the reactor. Water continuous dispersions of water-soluble polymers are free flowing liquids with product viscosities of from about 50 to about 10,000 centipoise (cP), as measured at low shear.

Additional inorganic salts may be used in combination with the ammonium salts for preparing the polymer dispersion including inorganic or organic sulfates, phosphates, chlorides, fluorides, citrates, acetates, tartrates, hydrogenphosphates and mixtures thereof. Representative additional inorganic salts include, sodium sulfate, magnesium sulfate, aluminum sulfate, sodium hydrogen phosphate, potassium hydrogen phosphate, sodium chloride, and the like.

Additional cationic salts may be used in combination with the above inorganic salts for preparing dispersions of anionic polymers. Representative cationic salts include tetraalkylammonium halides having from 4 to 22 carbon atoms, substituted tetraalkylammonium halides having from 4 to 22 carbon atoms, aryl trialkylammonium halides having from 9 to 22 carbon atoms, and substituted aryl trialkylammonium halides having from 9 to 22 carbon atoms.

Cationic polymer dispersions may also be prepared using a mixture of the inorganic salts described above with one or more anionic inorganic salts and one or more thiocyanates, perchlorates, chlorates, bromides, iodides or nitrates, including sodium, potassium or ammonium thiocyanate, sodium perchlorate, sodium chlorate, sodium bromide, sodium iodide, sodium nitrate and the like.

Representative anionic salts include metal or ammonium salts of trichloroacetate and trifluoromethanesulfonate; sulfonates and disulfonates such as methanesulfonate, ethanesulfonate, propanesulfonate, butanesulfonate, butanedisulfonate, pentanesulfonate, hexanesulfonate, hexanedisulfonate, and octanedisulfonate; aryl and substituted aryl sulfonates and disulfonates such as benzenesulfonate, nitrobenzenesulfonate, xylenesulfonate, toluenesulfonate, benzenedisulfonate, naphthalenesulfonate; dialkylsulfosuccinates such as diisobutylsulfosuccinate, diisooctylsulfosuccinate, dimethylsulfosuccinate, diethylsulfosuccinate, and diisopropylsulfosuccinate; dicycloalkylsulfosuccinates; and diarylsulfosuccinates. Preferred anionic salts include sodium hexanesulfonate, sodium benzenesulfonate, sodium xylenesulfonate sodium benzenedisulfonate, sodium butanedisulfonate, sodium hexanedisulfonate, sodium octanedisulfonate, and sodium decanedisulfonate. The relatively hydrophobic nature of these salts facilitate dispersion formation. Such salts may be added in any order with the other reaction components, and the order of addition can be used to effect changes in polymer processing.

Suitable polymeric stabilizing agents for preparing cationic and nonionic polymeric dispersions include water-soluble cationic polymers that are preferably soluble in the aqueous ammonium salt solution. The stabilizer is used in an amount of from about 1 to about 10% by weight based on the total weight of the polymer dispersion. The polymeric stabilizing agents or stabilizers facilitate discrete particle formation and prevent agglomeration and gel formation.

Suitable cationic stabilizers for preparing cationic and nonionic polymer dispersions include but are not limited to homopolymers of cationic diallyl-N,N-disubstituted ammonium monomers, homopolymers of N,N-disubstituted-aminoethyl(meth)acrylate monomers and their quaternary salts, homopolymers of N,N-disubstituted-aminopropyl(meth)acrylamide and their quaternary salts, copolymers of diallyl-N,N-disubstituted ammonium monomers and N,N-disubstituted-aminoethyl(meth)acrylate monomers and their quaternary salts, copolymers of diallyl-N,N-disubstituted ammonium monomers and N,N-disubstituted-aminopropyl(meth)acrylamide monomers and their quaternary salts and cationic polymers comprising at least 20 mole percent of one or more cationic diallyl-N,N-disubstituted ammonium monomers, N,N-disubstituted-aminoethyl(meth)acrylate monomers and their quaternary salts or N,N-disubstituted-aminopropyl(meth)acrylamide monomers and their quaternary salts and one or more nonionic monomers, preferably (meth)acrylamide, N-substituted or N,N-disubstituted (meth)acrylamide or styrene, and mixtures thereof. The molecular weight of the stabilizer is preferably in the range of about 10,000 to 10,000,000 g/mol.

Stabilizers used for preparing anionic and nonionic polymer dispersions include anionically charged water soluble polymers having a molecular weight of from about 10,000 to about 10,000,000 and preferably from about 1,000,000 to about 3,000,000. The stabilizer polymer must be soluble or slightly soluble in the salt solution, and must be soluble in water.

Representative anionic stabilizers include but are not limited to polyacrylic acid, poly(meth)acrylic acid, poly(2-acrylamido-2-methyl-1-propanesulfonic acid), copolymers of 2-acrylamido-2-methyl-1-propanesulfonic acid and an anionic comonomer selected from acrylic acid and methacrylic acid, polymers of one or more anionic monomers and one or more nonionic monomers, and the sodium salts of the aforementioned anionic stabilizers.

Nonionic dispersants can also be used alone or in combination with the cationic, anionic and nonionic stabilizers described herein for preparing cationic, anionic, nonionic and Zwitterionic polymer dispersions. Representative nonionic dispersants include, but are not limited to polyvinyl alcohol, polyvinyl pyrrolidinone, polyethylene glycol, polypropylene glycol, polyethylene oxide, polyethylene, soluble starch, epichlorohydrin/dimethylamine, poly(N-vinylpyridine), and the like.

A multifunctional alcohol such as glycerin or ethylene glycol may also be included in the polymerization system. The deposition of the fine particles is smoothly carried out in the presence of these alcohols.

The polymerization reaction is initiated by any means that results in generation of a suitable free radical. Initiation may be induced through the use of any number of conventional systems including thermal, photochemical, or redox coupled initiation systems. Thermally derived radicals, in which the radical species results from thermal, homolytic dissociation of a water-soluble azo, peroxide, hydroperoxide and perester compound are preferred. Especially preferred initiators are azo compounds including 2,2'-azobis(2-amidinopropane) dihydrochloride and 2,2'-azobis(N,N'-dimethyleneisobutylamine) hydrochloride, and the like.

A seed polymer may be added to the reaction mixture before the initiating polymerization of the monomers for the purpose of facilitating a fine dispersion of particles. The seed polymer is a water-soluble polymer insoluble in the aqueous solution of the polyvalent anionic salt. The monomer composition of the seed polymer need not be identical to that of the water-soluble polymer formed during polymerization. The seed polymer is preferably a polymer prepared by the dispersion polymer process described herein.

In alternative embodiments, the aqueous dispersion of one or more polymers in aqueous ammonium salt solution may be prepared by dispersing a preformed polymer in aqueous ammonium salt solution. The preformed polymer may be prepared by any of the polymerization methods known in the art including powder, latex or solution polymerization techniques.

Suitable ammonium salts used in preparing the polymer-ammonium salt formulation include any ammonium salt capable of reacting with the chlorine source to form chloramines under the conditions described herein. In an embodiment, the ammonium salt is selected from ammonium sulfate, ammonium chloride, ammonium bromide, ammonium hydrogen phosphate, ammonium acetate, ammonium formate, ammonium thiocyanate, ammonium persulfate, ammonium hydroxide and mixtures thereof.

In another embodiment, the ammonium salt is selected from ammonium sulfate, ammonium bromide, ammonium chloride and mixtures thereof.

In another embodiment, the ammonium salt is ammonium sulfate.

The amount of ammonium salts in the polymer dispersion is the amount sufficient to produce a molar ratio of chlorine (as $Cl_2$) to ammonium ion of about 1:10 to about 10:1.

In an embodiment, the amount of ammonium salts in the polymer dispersion is the amount sufficient to produce a molar ratio of chlorine (as $Cl_2$) to ammonium ion of about 1:3 to about 3:1.

In another embodiment, the amount of ammonium salts in the polymer dispersion is the amount sufficient to produce a molar ratio of chlorine (as $Cl_2$) to ammonium ion of about 1:1.

The level of polymer actives relative to ammonium salts in the polymer-ammonium salt formulation can be adjusted to optimum levels based on the dosing needs and desired product or process results.

The ammonium salt level in the polymer-ammonium salt formulation can be adjusted up relative to polymer by addition of aqueous ammonium salt solution to the produced polymer at a concentration of ammonium salt higher than that contained in the polymer or polymer-ammonium salt formulation. The ammonium salt level can be adjusted down relative to polymer by addition of an more dilute aqueous ammonium salt solution, water, polymer or other diluents to result in a concentration of ammonium salt lower than contained in the initial polymer-ammonium salt formulation.

In the case of dispersion polymers as described herein, the relative amounts of polymer actives and ammonium salts can be obtained by adjusting the level of the two components at the time of polymer manufacture and/or after polymerization as described above.

To prepare the antimicrobial composition, the polymer-ammonium salt formulation and chlorine source are mixed with sufficient alkali to result in a composition which exhibits effective antimicrobial activity in a system being treated, taking into account the pH and other parameters of the particular system.

In an embodiment, sufficient alkali is used to prepare a composition having a pH of at least about 7. In another embodiment, sufficient alkali is used to prepare a composition having a pH of at least about 10. In another embodiment, sufficient alkali is used to prepare a composition having a pH of at least about 12.

In an embodiment, the alkali is aqueous sodium hydroxide.

To prepare the antimicrobial compositions, the polymer-ammonium salt formulation, the alkali and the chlorine source may be added individually or alternatively, the alkali may be formulated with the chlorine source or the polymer-ammonium salt formulation prior to mixing of the chlorine source and the polymer-ammonium salt formulation.

As discussed above, stabilized chlorine compositions are used for inhibiting the growth of microorganisms in aqueous systems. However, biocide addition alone is not always sufficient for deposit/microbial control in industrial process systems. The addition of polymers to improve process efficiencies along with biocides to reduce microbial fouling may improve system performance to a greater degree than either product alone can achieve.

Additionally, polymer function in some systems may be compromised in the presence of high microbial activity or biofilm formation. The coordinated application of polymer treatment and biocide helps to ensure proper polymer performance.

The high ammonium salt concentration found in many polymer product compositions is potentially wasted in the treatment process unless mixed with a chlorine source. This invention takes advantage of the ammonium salts in polymer products to deliver a dual benefit—polymer dosing and chlorine stabilization using a single product.

Use of the polymer-ammonium salt formulation described herein can eliminate the need for a separate treatment product to stabilize chlorine. This decreases product inventory, storage costs and dosing costs.

A wide variety of polymer chemistries, product forms and delivery systems are used in water treatment and papermaking systems. In particular, high molecular weight polyacrylamides are commonly used as process aids and water treatment agents in various industrial and municipal operations. These water-soluble polymers assist in removing suspended solids and contaminants and in effecting various types of separations.

The present invention is applicable to all industries that can employ polymers as process aids and in water treatment processes. For example, the different types of industrial processes in which the method of the present invention can be applied generally include raw water processes, waste water processes, industrial water processes, municipal water treatment, food and beverage processes, pharmaceutical processes, electronic manufacturing, utility operations, pulp and paper processes, mining and mineral processes, transportation-related processes, textile processes, plating and metal working processes, laundry and cleaning processes, leather and tanning processes, personal care formulation additives and paint processes.

The polymers used to prepare the antimicrobial composition may comprise nonionic, cationic, anioni, amphoteric or Zwitterionic polymers. The polymers and their molecular weight and charge density can be readily selected by one of skill in the art based on the performance desired in the particular system being treated.

In an embodiment, the aqueous system is a papermaking system.

The use of dispersion polymers in papermaking processes well documented. For example, the use of high molecular weight cationic polymers including \dimethylaminoethylacrylate methyl chloride quaternary salt (DMAEA-MCQ)/acrylamide copolymer and dimethylaminoethylacrylate methyl chloride quaternary salt (DMAEA-BCQ)/acrylamide copolymer in retention and drainage applications is described in U.S. Pat. Nos. 6,059,930, 6,007,679 and 6,171,505 B1.

High molecular weight anionic and nonionic polymers including polyacrylamide acrylic acid salts/acrylamide copolymer and sodium AMPS/acrylamide copolymer, are often beneficial for the use of increasing retention and drainage in papermaking as described in U.S. Pat. Nos. 6,331,229 B1 and 6,432,271 B1

Moderate molecular weight coagulant type polymers, such as diallyldimethylammonium chloride (DADMAC)/acrylamide copolymers, are useful in paper retention, drainage and process improvement applications as described in U.S. Pat. Nos. 6,071,379, and 6,238,521 B 1.

Combinations of lower and higher molecular weight polymers, modified solubilities and/or cationic and anionic charged polymers are used in papermaking processes. Examples can be found in U.S. Pat. No. 6,592,718 B1 and US Patent Application No. 2006/0084771.

High and moderate molecular weight cationic polymers, such as DMAEA-MCQ/acrylamide copolymer and DMAEA-BCQ/acrylamide copolymer are useful in coated broke treatment as described in U.S. Pat. Nos. 5,891,304 and 5,466,338.

High molecular weight cationic polymers such as copolymers of DMAEA-BCQ/acrylamide, or DMAEA-MCQ/acrylamide are useful in clarification and dewatering of paper mill waters and can be used alone or in combination with other additives such as microparticles as described in U.S. Pat. Nos. 5,938,937, 6,171,505 B1 and 6,413,433 B1.

High molecular weight anionic and nonionic polymers such as polyacrylamide or copolymers of acrylic acid salts/acrylamide or sodium AMPS/acrylamide, are often used for clarification and dewatering as discussed in U.S. Pat. No. 6,217,778 B1.

Moderate molecular weight coagulant type polymers, such as DADMAC/acrylamide copolymers, are useful in clarification of drinking process waters as described in U.S. Pat. No. 6,019,904. Use of the polymers in color removal of paper mill wastewater is described in U.S. Pat. Nos. 5,292,793, 5,435,922 and 6,258,279.

Structurally modified polymers of the type described in U.S. Pat. No. 6,605,674 B1 are useful in the papermaking process as well as in paper wastewater treatment.

The chlorine source, the aqueous polymer-ammonium salt formulation, and the alkali may all be added to points in the stream of the process system which are the same, or spaced but typically adjacent to each other. If desired, the chlorine source and the alkali may be premixed and added to the stream of the process system together, and the aqueous polymer-ammonium salt formulation may be separately added to the stream of the process system, either at the same location or at a nearby location. As another option, the aqueous polymer-ammonium salt formulation and the alkali may be premixed and added to the stream of the process system together, and the chlorine source may be separately added to the stream of the process system, either at the same location or at a nearby location. Alternatively, the chlorine source, the aqueous polymer-ammonium salt formulation, and the alkali may each be separately added to the stream of the processing system, typically at the same or closely spaced points of the stream.

In an embodiment, the antimicrobial composition is prepared prior to adding to the system.

The chlorine source, aqueous polymer-ammonium salt formulation, alkali source, or any mixtures thereof may be added to the process system continuously or intermittently. The frequency and timing of addition may be controlled manually or by using control automation linked to timers or sensors that trigger addition based on process system conditions such as oxidation reduction potential, halogen residual, pH, microbial activity, deposit formation, or other system conditions.

For each addition method, the chlorine source, the aqueous polymer-ammonium salt formulation, and the alkali may be mixed prior to addition to the paper process system. The resulting stabilized product may be stored for a short period of time, and then added to the treated system when desired. Some polymers such as low charge cationic polymers such as acrylamide/DMAEA•MCQ, acrylamide/DMAEA•BCQ and acrylamide/DMAEM•MCQ are rapidly degraded at high pH, and require immediate dosing into the process system to retain full advantage of favorable polymer properties. Similarly, some loss of available chlorine occurs over time as the antimicrobial composition is stored. Therefore, immediate application of the mixture into the process system is preferred. As used herein, "immediate" means within one hour, preferably within 10 minutes of formation of the antimicrobial composition.

The frequency and duration of treatment and concentration of active ingredient needed in order to maintain adequate inhibition of microorganisms can be determined by one of skill in the art depending on the characteristics of the system being treated. Typically, a level of about 0.1 to about 100 ppm of chlorine (as $Cl_2$) is sufficient to exhibit effective control.

The foregoing may be better understood by reference to the following example, which is presented for purposes of illustration and is not intended to limit the scope of the invention.

EXAMPLE

Three experiments are performed, each with the objective of evaluating the ability of a representative polymer-ammonium salt formulation to stabilize chlorine from sodium hypochlorite. In this example, the polymer-ammonium salt formulation is an DADMAC/acrylamide dispersion copolymer in aqueous ammonium sulfate solution having an RSV of 2.26, available from Nalco Company, Naperville, Ill.

Series #1 uses low reactant concentrations of 0.005 molar. Series #2 uses 10-fold higher reactant concentration of 0.05 molar. Series #3 uses the higher reactant concentrations of series #2 along with added sodium hydroxide.

Each series includes two controls: A (chlorine and water); B (chlorine and ammonium sulfate); and a reaction C using chlorine and a representative polymer-ammonium salt formulation.

In each case the concentration of chlorine (as $Cl_2$) and ammonium sulfate are blended in equimolar ratio. Ammonium sulfate concentrations in the control and polymer-ammonium salt formulation are equivalent.

After performing each reaction, the product pH is measured. The concentrations of free and stabilized halogen and total reaction yield are determined using N,N-diethyl-p-phenylenediamine (DPD) reagent. In each set of experiments, 100% yield is determined by measuring the total residual oxidant (TRO) of Reaction "A" in which no halogen stabilizer is present. Residual oxidant values in each product are reported in ppm, and also as a percent yield compared to reactions with no stabilizer. Results are shown in Table 1. Reaction yields are shown in brackets.

organisms that infest papermaking systems, wherein the antimicrobial composition is prepared prior to adding to the system, wherein the pH is at least 7 and wherein the polymer-ammonium salt reacts with the converted chlorine such that the resulting composition displays less than 10% oxidant loss and more than 80% of the oxidant persists in a stabilized form for at least 3 minutes.

TABLE 1

Free and Stabilized Chlorine Reaction Products Resulting from Mixtures of a Polymer-Ammonium Salt Formulation and Sodium Hypochlorite.

| Series | Reaction Mixture | Reactant Conc. | pH | FRO | 3FRO | TRO | 3TRO |
|---|---|---|---|---|---|---|---|
| 1A | NaOCl + water | 0.005M Chlorine | 9.4 | 384 [100%] | 386 [101%] | 384 [100%] | N.D |
| 1B | NaOCl + ammonium sulfate | 0.005M chlorine and 0.005M (NH$_4$)$_2$SO$_4$ | 7.5 | 170 [44%] | 388 [101%] | 388 [101%] | N.D. |
| 1C | NaOCl + polymer dispersion | 0.005M chlorine and 0.005M (NH$_4$)$_2$SO$_4$ | 7.2 | 122 [32%] | 388 [101%] | 386 [101%] | N.D. |
| 2A | NaOCl + water | 0.05M Chlorine | 10.3 | 3780 [98%] | 3800 [98%] | 3860 [100%] | 3860 [100%] |
| 2B | NaOCl + ammonium sulfate | 0.05M chlorine and 0.05M (NH$_4$)$_2$SO$_4$ | 8.0 | 660 [17%] | 3680 [95%] | 3860 [100%] | 3860 [100%] |
| 2C | NaOCl + polymer dispersion | 0.05M chlorine and 0.05M (NH$_4$)$_2$SO$_4$ | 6.0 | 360 [9%] | 960 [25%] | 1460 [38%] | 2380 [62%] |
| 3A | NaOCl + NaOH + water | 0.05M chlorine and 0.25% NaOH | 12.7 | 3760 [97%] | 3780 [98%] | 3840 [99%] | 3840 [99%] |
| 3B | NaOCl + NaOH + ammonium sulfate | 0.05M chlorine and 0.25% NaOH and 0.05M (NH$_4$)$_2$SO$_4$ | 12.6 | 400 [107%] | 2880 [73%] | 3940 [101%] | 3920 [102%] |
| 3C | NaOCl + NaOH + polymer dispersion | 0.05M chlorine and 0.25% NaOH and 0.05M (NH$_4$)$_2$SO$_4$ | 12.3 | 620 [16%] | 3540 [92%] | 3600 [93%] | 3580 [93%] |

Oxidant Residuals Measured using DPD:
FRO = ppm Free Residual Oxidant in reaction [% of total oxidant].
3FRO = ppm Free Residual Oxidant in reaction [% of total oxidant], with 3-minute DPD reaction time.
TRO = ppm Total Residual Oxidant in reaction [% of total oxidant].
3TRO = ppm Total Residual Oxidant in reaction [% of total oxidant], with 3-minute DPD reaction time.

This example demonstrates that the polymer-ammonium salt formulation reaction with chlorine results in only a small amount of oxidant loss (>90% oxidant recovery), with >80% of the oxidant in a stabilized form expected to have good antimicrobial properties.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. A method of inhibiting growth of microorganisms in an aqueous system comprising treating the system with an effective inhibiting amount of an antimicrobial composition, the antimicrobial composition comprising one or more ammonium salts and a nonionic dispersant to form an aqueous polymer-ammonium salt dispersion comprising one or more polymers linked to one or more ammonium salts, and mixing the aqueous polymer-ammonium salt dispersion with a chlorine source in a molar ratio of chlorine (as Cl$_2$) to ammonium ion of about 1:10 to about 10:1 relative to the amount of chlorine present after complete conversion of the chlorine source and sufficient alkali to result in a composition which exhibits effective antimicrobial activity in an industrial water system being treated, wherein the aqueous system is a papermaking system and the microorganisms are the sort of microorganisms that infest papermaking systems, wherein the antimicrobial composition is prepared prior to adding to the system, wherein the pH is at least 7 and wherein the polymer-ammonium salt reacts with the converted chlorine such that the resulting composition displays less than 10% oxidant loss and more than 80% of the oxidant persists in a stabilized form for at least 3 minutes.

2. The method of claim 1 wherein said polymers have a weight average molecular weight greater than 100,000 g/mole.

3. The method of claim 2 wherein said chlorine source is selected from the group consisting of chlorine gas and sodium hypochlorite.

4. The method of claim 1, wherein the composition has a pH of at least 7.

5. The method of claim 4 wherein said ammonium salt is selected from the group consisting of ammonium sulfate, ammonium chloride, ammonium bromide, ammonium acetate, ammonium formate, ammonium thiocyanate, ammonium hydroxide and mixtures thereof.

6. The method of claim 5 wherein said dispersion of one or more polymers in an aqueous ammonium salt solution has a reduced specific viscosity in 1 N NaNO$_3$ solution of about 0.5 to about 30 dL/g.

7. The method of claim 6, wherein the composition has a pH greater than 10.

8. The method of claim 7 wherein said ammonium salt is selected from the group consisting of ammonium sulfate, ammonium bromide, ammonium chloride and mixtures thereof.

9. The method of claim 8 wherein the molar ratio of chlorine (as Cl$_2$) to ammonium ion of about 1:3 to about 3:1 relative to the amount of chlorine present after complete conversion of the chlorine source.

10. The method of claim 9 wherein said composition further comprises a substance selected from the group consisting of copolymers of (meth)acrylamide and one or more monomers selected from diallyldimethylammonium chloride, dimethylaminoethyl (meth)acrylate methyl chloride quaternary salt, dimethylaminoethyl (meth)acrylate benzyl chloride quaternary salt, (meth)acrylic acid and its salts and 2-acrylamido-2-methylpropanesulfonic acid.

11. The method of claim 10 wherein said substance has a charge of about 2 to about 30 mole percent.

12. The method of claim 11 wherein said ammonium salt is ammonium sulfate.

13. The method of claim 12 wherein the molar ratio of chlorine (as $Cl_2$) to ammonium ion of about 1:1 relative to the amount of chlorine present after complete conversion of the chlorine source.

14. The method of claim 13, wherein the composition has a pH greater than 12.

15. The method of claim 1 wherein said ammonium salt is selected from the group consisting of ammonium sulfate, ammonium bromide, ammonium chloride and mixtures thereof.

* * * * *